US012673636B2

(12) United States Patent
Obert et al.

(10) Patent No.: US 12,673,636 B2
(45) Date of Patent: Jul. 7, 2026

(54) SEATBELT ATTACHMENT FOR SURGICAL PATIENT

(71) Applicant: Ford Global Technologies, LLC, Dearborn, MI (US)

(72) Inventors: Emily Obert, Ferndale, MI (US); Rima Shkoukani, Troy, MI (US); Christopher Klein, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 18/887,458

(22) Filed: Sep. 17, 2024

(65) Prior Publication Data

US 2026/0077737 A1     Mar. 19, 2026

(51) Int. Cl.
*A61F 5/30* (2006.01)
*B60R 22/00* (2006.01)
*B60R 22/14* (2006.01)

(52) U.S. Cl.
CPC .............. B60R 22/14 (2013.01); A61F 5/30 (2013.01); *B60R 2022/006* (2013.01)

(58) Field of Classification Search
CPC ...... A61F 5/00; A61F 5/01; A61F 5/30; A61F 5/32; A61F 5/37; A61F 5/3769; A61F 5/3776; A61F 5/3784; A61F 5/3792; B60R 22/12; B60R 22/14; B60R 2022/006
USPC ...................................... 280/801.1, 805, 808
See application file for complete search history.

(56) References Cited

U.S. PATENT DOCUMENTS

| | | | | |
|---|---|---|---|---|
| 4,786,080 A | * | 11/1988 | Jay ......................... | B60R 22/14 |
| | | | | 280/808 |
| 4,795,190 A | * | 1/1989 | Weightman ............. | B60R 22/00 |
| | | | | 280/808 |
| 5,161,824 A | * | 11/1992 | Li ........................... | B60R 22/14 |
| | | | | 280/808 |
| 5,584,536 A | | 12/1996 | White | |
| 5,664,843 A | | 9/1997 | Gleason | |
| 6,174,032 B1 | * | 1/2001 | Conaway ............... | B60N 2/265 |
| | | | | 297/483 |
| 6,273,467 B1 | | 8/2001 | Berke et al. | |

(Continued)

FOREIGN PATENT DOCUMENTS

| | | |
|---|---|---|
| ES | 1275080 U | 7/2021 |
| JP | 2002046575 A | 2/2002 |
| KR | 20120007167 U | 10/2012 |

*Primary Examiner* — Jason D Shanske
*Assistant Examiner* — Daniel M. Keck
(74) *Attorney, Agent, or Firm* — Frank A. MacKenzie; Brooks Kushman P.C.

(57) ABSTRACT

A seatbelt attachment for attachment to a webbing of a seatbelt assembly of a vehicle includes a chest section and a shoulder section. The chest section has a chest-section axis on which the chest section is elongated, and the shoulder section has a shoulder-section axis on which the shoulder section is elongated. A joint connects the chest section and the shoulder section. The joint is flexible relative to the chest section and the shoulder section. The joint has a rotational axis that is transverse to the chest-section axis and the shoulder-section axis. The shoulder section includes a back elongated along the axis. The shoulder section includes two legs elongated along the chest-section axis and aligned along the chest-section axis with the back. The legs each have a distal end and the legs extend from the back to the distal ends, respectively.

20 Claims, 6 Drawing Sheets

(56) References Cited

U.S. PATENT DOCUMENTS

| 6,557,895 | B2 | | 5/2003 | Haack et al. | |
|---|---|---|---|---|---|
| 9,010,808 | B2 | | 4/2015 | Kampondeni | |
| 2015/0314711 | A1 | * | 11/2015 | Mitsuo ................ | B60R 22/105 |
| | | | | | 297/482 |

* cited by examiner

SEATBELT ATTACHMENT FOR SURGICAL PATIENT

BACKGROUND

Vehicles are equipped with seatbelt assemblies each including a seatbelt retractor and webbing retractably payable from the seatbelt retractor. The seatbelt assembly may include an anchor coupled to the webbing, and a latch plate that engages a buckle. The webbing may extend continuously from the seatbelt retractor to the anchor. The webbing may be fabric, e.g., woven polyester. The clip slides freely along the webbing and, when engaged with the buckle, divides the webbing into a lap belt and a shoulder belt.

The seatbelt retractor is moveable from an unlocked position to a locked position. In the locked position, the seatbelt retractor prevents extension of the webbing to limit the forward movement of the occupant. The seatbelt retractor may change from the unlocked position to the locked position during a sudden deceleration of the vehicle, i.e., deceleration triggers components of the seatbelt retractor to change from the unlocked position to the locked position.

The shoulder belt extends across the chest of the occupant. For recipients of recent surgery, the shoulder belt may extend across a healing incision. Examples of surgeries that may use an incision in the area across which a shoulder belt extends includes a mastectomy, heart-related surgeries, etc. In such examples, the healing incision may be tender and extension of the shoulder belt across the incision may cause uncomfortable pressure and/or rubbing on the area of the incision.

DETAILED DESCRIPTION

Figure 1:
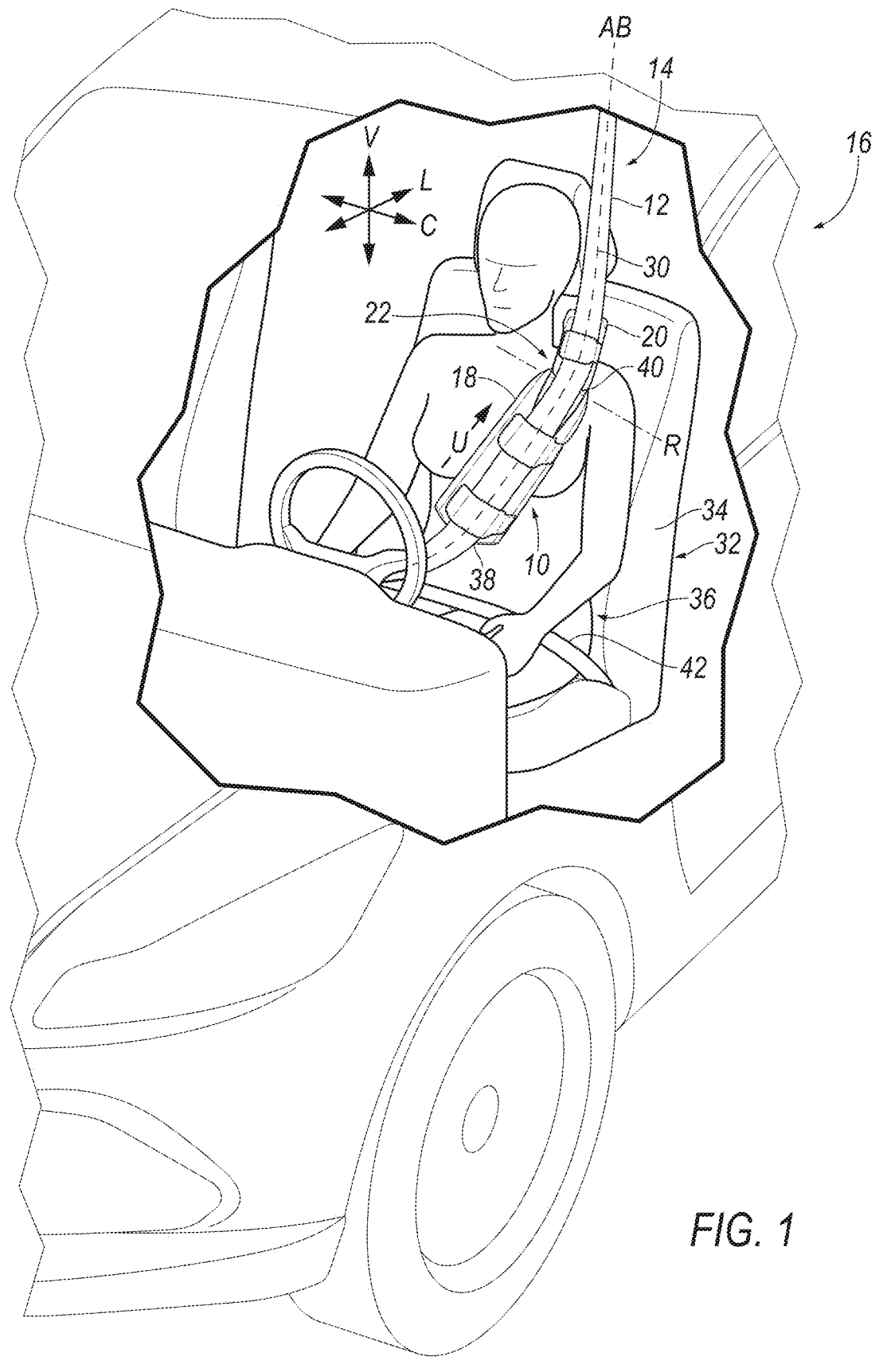
FIG. 1 is a cut-away view of a vehicle showing a seatbelt assembly with a seatbelt attachment engaged with a shoulder belt.
Figure 2:
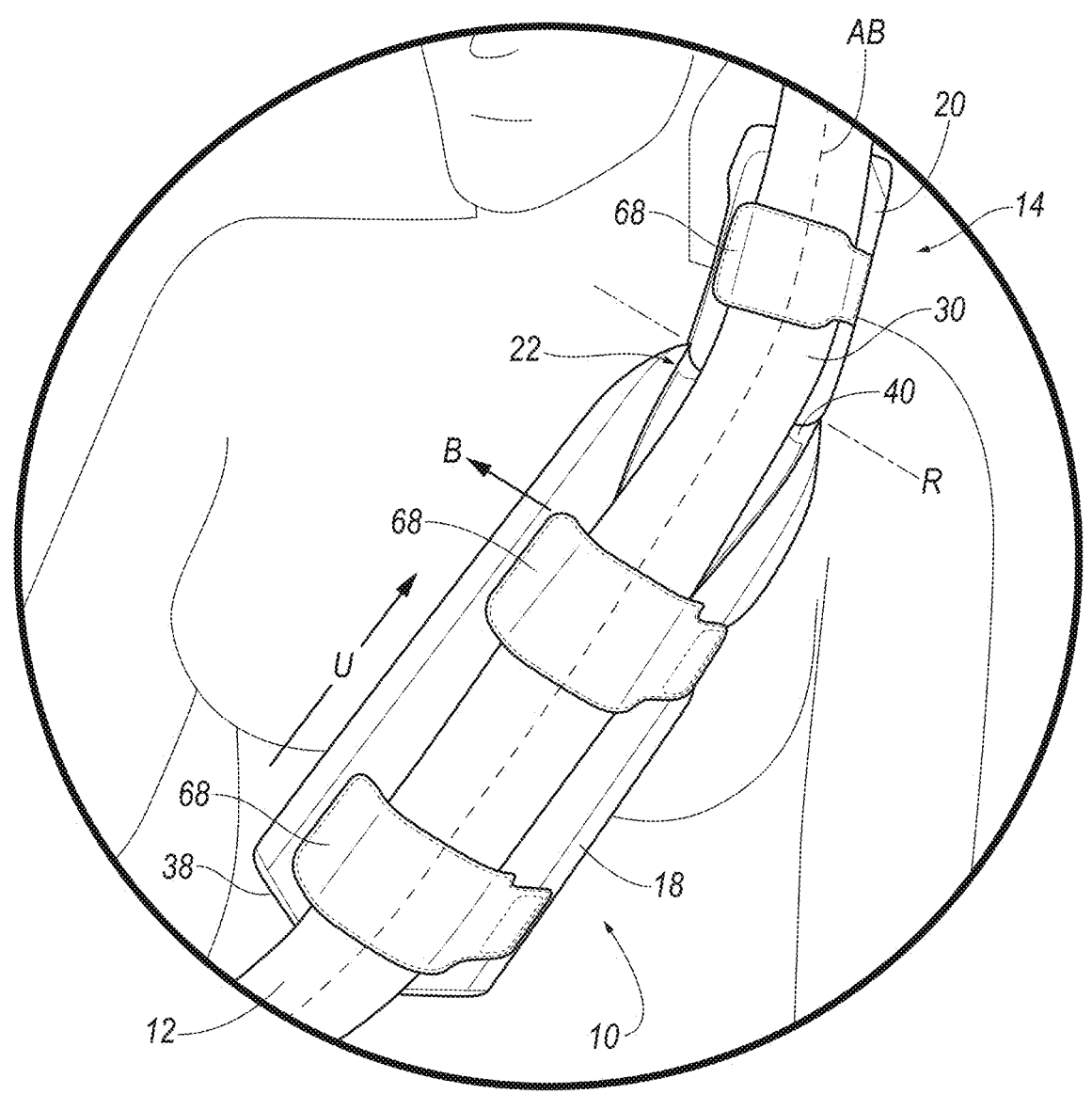
FIG. 2 is a magnified view of a portion of FIG. 1.

With reference to the Figures, wherein like numerals indicate like parts throughout the several views, a seatbelt attachment 10 for attachment to a webbing 12 of a seatbelt assembly 14 of a vehicle 16 is generally shown. The seatbelt attachment 10 includes a chest section 18 and a shoulder section 20. The chest section 18 has a chest-section axis AC on which the chest section 18 is elongated, and the shoulder section 20 has a shoulder-section axis AS on which the shoulder section 20 is elongated. A joint 22 connects the chest section 18 and the shoulder section 20. The joint 22 is flexible relative to the chest section 18 and the shoulder section 20. The joint 22 has a rotational axis R that is transverse to the chest-section axis AC and the shoulder-section axis AS. The shoulder section 20 includes a back 24 elongated along the chest-section axis AC. The shoulder section 20 includes two legs 26 elongated along the chest-section axis AC and aligned along the chest-section axis AC with the back 24. The legs 26 each have a distal end 28 and the legs 26 extend from the back 24 to the distal ends 28, respectively.

An example seatbelt assembly 14 includes the seatbelt attachment 10. The seatbelt assembly 14 includes webbing 12. The webbing 12 includes a shoulder belt 30 elongated along a shoulder-belt axis AB. The seatbelt attachment 10 is releasably engageable with the shoulder belt 30.

The seatbelt attachment 10 is designed to maintain the placement of the seatbelt attachment 10 in position relative to an occupant to reduce the likelihood of rubbing and unwanted compression on the occupant, especially in examples in which the occupant is a recent surgical patient with a healing incision from surgery on their chest. Since the joint 22 is flexible relative to the chest section 18 and the shoulder section 20, the chest section 18 can be seated on the chest of the occupant and the shoulder section 20 can bend along the shoulder of the occupant, keeping the shoulder belt 30 spaced from the chest of the occupant, e.g., a healing incision on the chest. The joint 22 allows the seatbelt attachment 10 to follow contours of the occupant along a length of the seatbelt attachment 10, including contours of different body types of different occupants.

The legs 26 and the back 24 of the shoulder section 20 space the shoulder belt 30 from the chest of the occupant, e.g. from a healing incision left from surgery. The legs 26 can be positioned at a comfortable location on the chest of the occupant relative to a healing incision, e.g., to avoid direct contact with the incision.

With reference to FIG. 1, the vehicle 16 may be any suitable type of ground vehicle, e.g., a passenger or commercial automobile such as a sedan, a coupe, a truck, a sport utility, a crossover, a van, a minivan, a taxi, a bus, etc. The vehicle 16 defines a vehicle-longitudinal axis L extending between a front end (not numbered) and a rear-end (not numbered) of the vehicle 16. The vehicle 16 defines a cross-vehicle axis C extending cross-vehicle from one side to the other side of the vehicle 16. The vehicle 16 defines a vertical axis V extending through a floor and ceiling of the vehicle 16. The vehicle-longitudinal axis L, the cross-vehicle axis C, and the vertical axis V are perpendicular relative to each other. The vehicle 16 includes a vehicle 16 frame (not numbered) and a vehicle 16 body (not numbered). The vehicle 16 frame and/or the vehicle 16 body defines a passenger compartment (not numbered) to house occupants of the vehicle 16. The passenger compartment may extend across the vehicle 16, i.e., from one side to the other side of the vehicle 16. The passenger compartment includes a front and a rear.

The vehicle 16 includes one or more seats 32 in the passenger compartment. The seats 32 may be arranged in any suitable manner in the passenger compartment. The seats 32 may be of any suitable type, e.g., a bucket seat, bench seat, etc.

The seat 32 includes a seatback 34 and a seat bottom. The seatback 34 may be supported by the seat bottom and may be stationary or movable relative to the seat bottom. The seatback 34 and the seat bottom may be adjustable in multiple degrees of freedom. Specifically, the seatback 34 and the seat bottom may themselves be adjustable, in other words, adjustable components within the seatback 34 and/or the seat bottom, and/or may be adjustable relative to each other.

The seatback 34 may include a seatback frame and a covering 52 supported on the seatback frame. The seatback frame may include tubes, beams, etc. The covering 52 may include upholstery. The upholstery may be cloth, leather, faux leather, or any other suitable material.

The seatback 34 may define an occupant seating area 36. The occupant may be disposed in the occupant seating area 36, as shown in the Figures. The occupant seating area 36 may be on a front side of the seatback 34.

The vehicle 16 includes one or more seatbelt assemblies 14. The seatbelt assemblies 14 include a seatbelt retractor and the webbing 12 extendable from the seatbelt retractor. The vehicle 16 may include any suitable number of seatbelt assemblies 14, for example, one seatbelt assembly 14 for each seat 32. In the example shown in the Figures, one seat 32 at a front-left position is shown to include the seatbelt assembly 14, and any seat 32 in any position in the passenger compartment may include the seatbelt assembly 14. The seatbelt attachment 10 may be selectively attached to and removed from any one of the seatbelt assemblies 14 that has a shoulder belt 30.

The seatbelt assembly 14, when fastened, is designed to control the kinematics of the occupant during certain vehicle 16 impacts or sudden stops. The seatbelt assembly 14 may include an anchor coupled to the webbing 12, and a clip that engages a buckle. Each seatbelt assembly 14 may be disposed adjacent to one of the seats. The seatbelt assembly 14, when fastened, is designed to control certain kinematics of the occupant during certain vehicle 16 impacts or sudden stops. The seatbelt assembly 14 may be a three-point harness, meaning that the webbing 12 is attached at three points around the occupant when fastened. The seatbelt assembly 14 may, alternatively, include another arrangement of attachment points.

The webbing 12 may extend continuously from the seatbelt retractor to the anchor. The seatbelt retractor provides payout and retraction of the webbing 12, e.g., via rotation of the spool. The seatbelt retractor may be mounted at any suitable location in the vehicle 16. One end of the webbing 12 feeds into the seatbelt retractor, and the other end of the webbing 12 is fixed to the anchor. The anchor may, for example, be fixed to the seat and/or to the vehicle 16 body, e.g., the pillar, the floor, etc. The webbing 12 may be fabric, e.g., polyester. The clip slides freely along the webbing 12 and, when engaged with the buckle, divides the webbing 12 into a lap belt 42 and a shoulder belt 30. In such an example, the lap belt 42 extends across the lap of the occupant, e.g., from the anchor to the clip, and the shoulder belt 30 extends in an upward direction U from the lap belt 42, e.g., from the clip to the retractor. The seatbelt assembly 14 may be, as an example, a conventional type.

The shoulder belt 30 has a shoulder-belt axis AB, as introduced above, and is elongated along the shoulder-belt axis AB, i.e., the longest dimension of the shoulder belt 30 is along the shoulder-belt axis AB. The shoulder-belt axis AB of the shoulder belt 30 is a central line that longitudinally bisects the shoulder belt 30. The shoulder-belt axis AB of the shoulder belt 30 may curve. For example, the shoulder belt 30 may curve around the torso of the occupant when the seatbelt assembly 14 is buckled, in which case the shoulder-belt axis AB of the shoulder belt 30 curves. The shoulder belt 30 is flexible relative to the torso of the occupant, and accordingly, the shoulder-belt axis AB moves as the shoulder belt 30 moves.

As set forth above, the seatbelt attachment 10 includes a chest section 18 extending along the shoulder-belt axis AB and a shoulder section 20 extending along the shoulder-belt axis AB. The joint 22 is between the chest section 18 and shoulder section 20 along the shoulder-belt axis AB. The chest section 18, the joint 22, and the shoulder section 20 are positioned consecutively. Specifically, the chest section 18, the joint 22, and the shoulder section 20 are consecutive along the shoulder-belt axis AB in the upward direction U. The chest section 18 and the joint 22 section may abut each other with the joint 22 therebetween, as shown in the example in the Figures.

The chest section 18 has a bottom end 38 and a top end 40. The bottom end 38 is between the top end 40 and the lap belt 42. The chest section 18 is elongated in an upward direction U along the shoulder-belt axis AB from the bottom end 38 to the top end 40. The shoulder section 20 extends in a direction away from the top end 40 of the chest section 18 in the upward direction U along the shoulder-belt axis AB. In the example shown in the Figures, the shoulder section 20 abuts the chest section 18 and extends from the chest section 18 in the upward direction U. The shoulder section 20 and the chest section 18 are end-to-end along the shoulder-belt axis AB.

Figure 3:
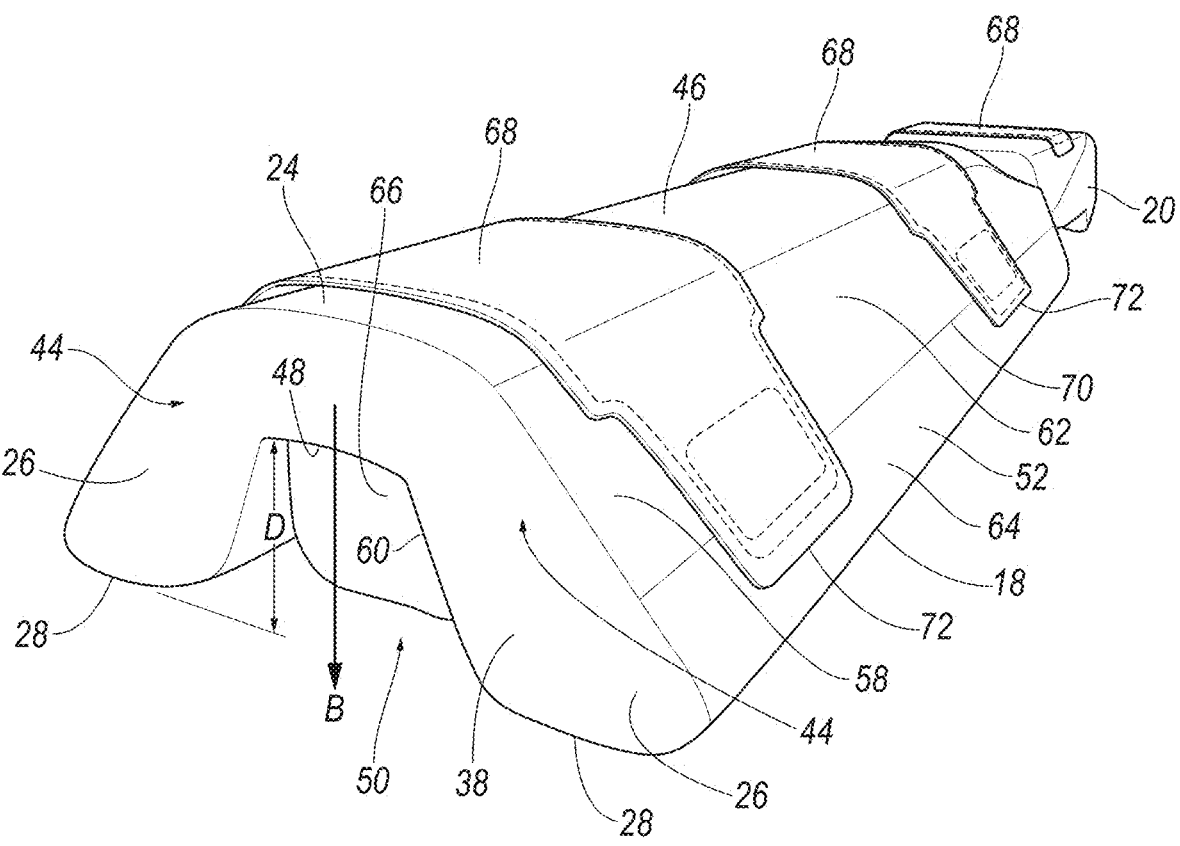
FIG. 3 is a perspective view of the seatbelt assembly.
Figure 4:
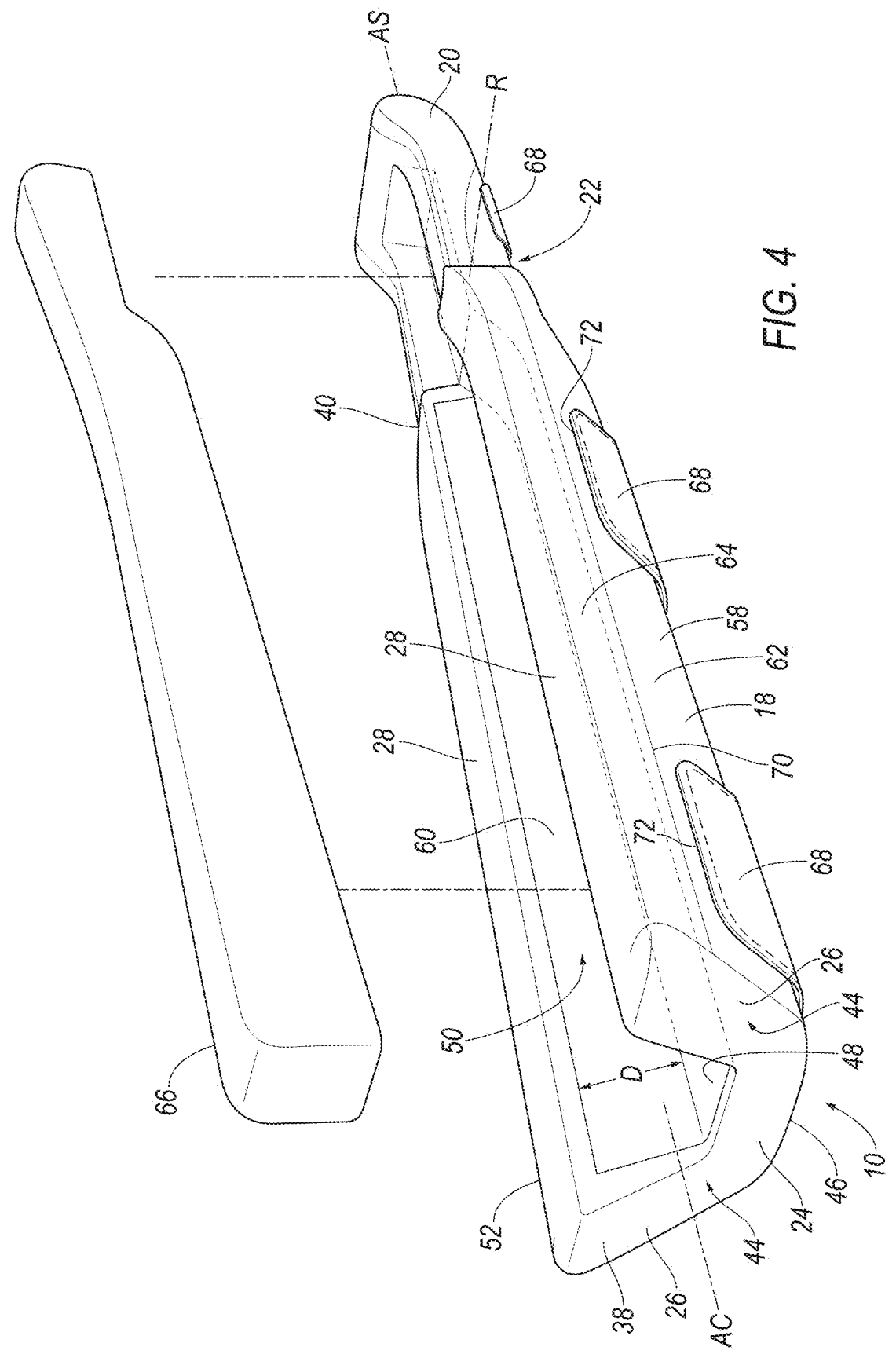
FIG. 4 is an exploded view of an example of the seatbelt assembly.
Figure 5:
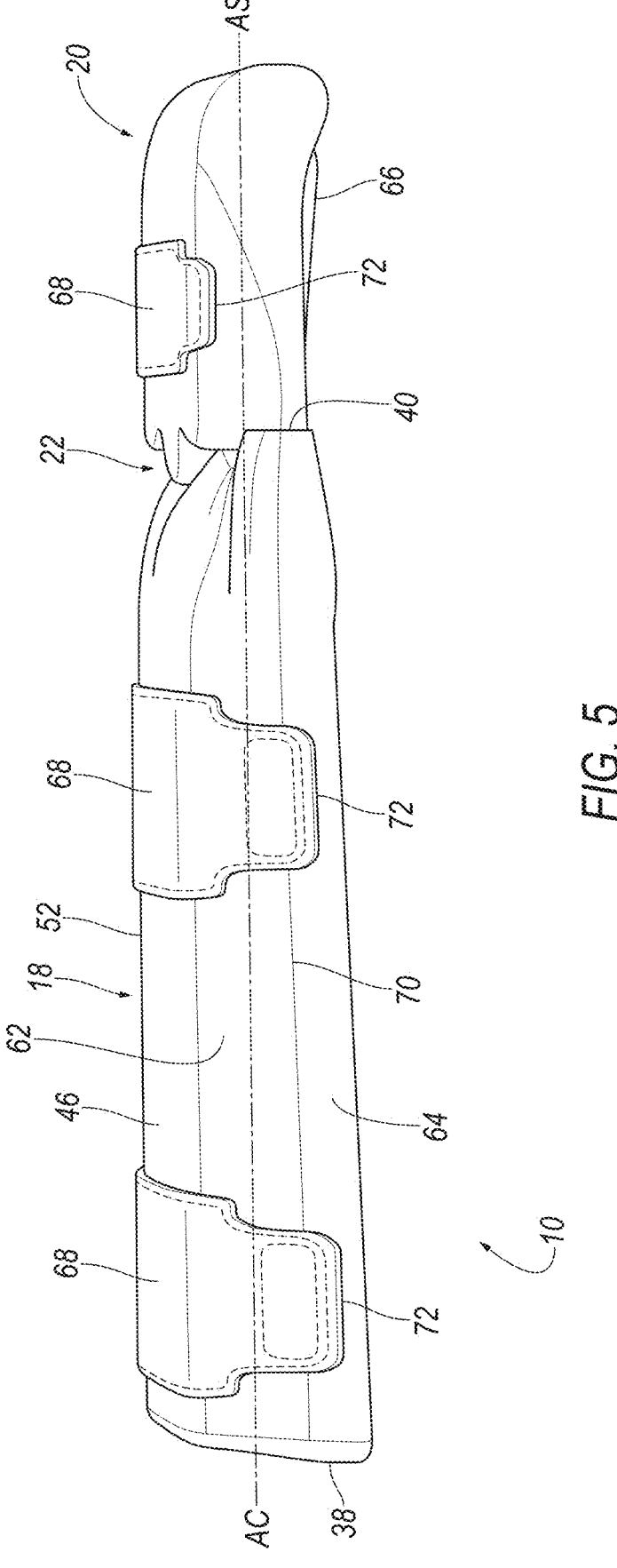
FIG. 5 is another perspective view of an example seatbelt assembly
Figure 6:
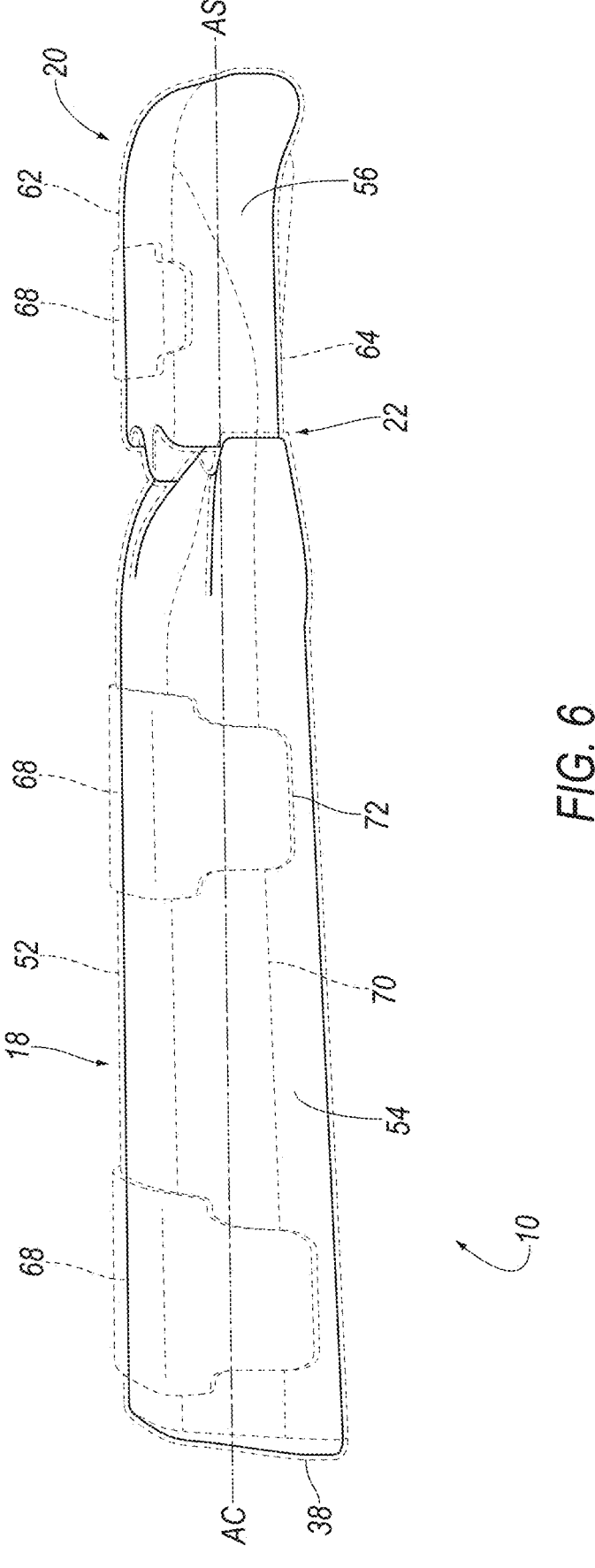
FIG. 6 is the perspective view of FIG. 5 with a covering shown in broken lines to show a first foam core and a second foam core.

As set forth above, the shoulder section 20 has a shoulder-section axis AS on which the shoulder section 20 is elongated, and the chest section 18 has a chest-section axis AC on which the chest section 18 is elongated. In other words, the longest dimension of the shoulder section 20 is along the shoulder-section axis AS, and the longest dimension of the chest section 18 is along the chest-section axis AC. The chest-section axis AC and the shoulder-section axis AS may be in a common plane. The joint 22 may allow the shoulder section 20 and the chest section 18 to rotate to a position in which the shoulder-section axis AS and the chest-section axis AC are colinear, as shown for example in FIGS. 3 and 4.

The shoulder section 20 may be thinner than the chest section 18 in a direction away from the body of the occupant when the seatbelt attachment 10 is attached to the shoulder belt 30 and the seatbelt assembly 14 is buckled. The chest section 18 and the shoulder section 20 extend from the shoulder belt 30 in a body direction B. When the seatbelt attachment 10 is attached to the shoulder belt 30, the body direction B is the direction from the shoulder belt 30 toward the body. The shoulder section 20 may be thinner than chest section 18 in the body direction B, as shown in the example in the Figures. The shoulder section 20 may have a flat surface at the shoulder belt 30. A surface of the shoulder section 20 facing the body of the occupant may be, for example, concave. In other examples, the surface of the shoulder section 20 facing the body of the occupant may be flat.

The length of the chest section 18 along the chest-section axis AC is longer than the length of the shoulder section 20 along the shoulder-section axis AS. As an example, the length of the chest section 18 along the chest-section axis AC may be more than three times longer than the length of the shoulder section 20 along the shoulder-section axis AS.

The shoulder section 20 includes a back 24 elongated along the shoulder-section axis AS, i.e., the longest dimension of the back 24 is along the shoulder-section axis AS. The shoulder section 20 includes two legs 26 elongated along the shoulder-section axis AS, i.e., the longest dimension of each leg 26 is along the shoulder-section axis AS. The legs 26 aligned along the axis with the back 24. In other words, the legs 26 are side-by-side with the back 24. The back 24 and the legs 26 may each extend from the bottom end 38 to the top end 40 of the shoulder section 20. The legs 26 each have a proximal end 44 at the back 24 and a distal end 28. Each leg 26 is elongated along the proximal end 44 and the distal end 28 of the respective leg 26. Each leg 26 extends laterally from the back 24 to the respective distal end 28.

The back 24 includes an outer surface 46 and an inner surface 48 opposite the outer surface 46. When the seatbelt attachment 10 is attached to the shoulder belt 30, the outer surface 46 faces the shoulder belt 30 and the inner surface 48 faces away from the shoulder belt 30. When the seatbelt attachment 10 is attached to the shoulder belt 30, the inner surface 48 faces the chest of the occupant.

When the seatbelt attachment 10 is attached to the shoulder belt 30, the legs 26 extend from the back 24 of the shoulder section 20 toward seatback 34, i.e., toward the occupant when an occupant is on the seat 32. The distal ends 28 of the legs 26 may be spaced from each other defining a cavity 50 between distal ends 28. The cavity 50 is along the inner surface 48 of the back 24. The cavity 50 may be elongated along the shoulder-belt axis AB. The cavity 50 may extend from the bottom end 38 to the top end 40 of the shoulder section 20, as shown in the example in the Figures. As shown in the example of the Figures, the cavity 50 extends through the bottom end 38 and the top end 40 of the shoulder section 20. The occupant of the seat 32 may position the cavity 50 at a healing incision when the occupant places the seatbelt attachment 10 across the chest of the occupant while buckling the seatbelt assembly 14. This spaces the shoulder belt 30 from the healing incision to minimize or prevent compression and rubbing of the healing incision by the shoulder belt 30.

The legs 26 may be the same length as each other from the back 24 to the distal ends 28, respectively. The legs 26 may be spaced from each other at the back 24. The legs 26 may extend away from each other from the back 24 to the distal ends 28, respectively. In other words, the cavity 50 expands from the back 24 to the distal ends 28. In the example shown in the Figures, the legs 26 are the same length from the back 24 to the respective distal end 28, the legs 26 are spaced from each other at the back 24, and the legs 26 extend away from each other from the back 24 to the distal ends 28. In such an example, the cavity 50 is a trapezoidal channel. In other words, the back 24 and the legs 26 for an open-faced trapezoidal shape in cross section perpendicular to the shoulder-section axis AS.

The cavity 50 has a depth D from the back 24 to the distal ends 28. The depth D may be, for example, taken along a line centered between the legs 26. The depth D of the cavity 50 may taper in the upward direction U. In other words, the depth D of the cavity 50 may progressively decrease in cross sections taken perpendicular to the shoulder-section axis AS spaced from each other in the upward direction U.

The seatbelt attachment 10 includes at least one body and a covering 52 over the body. For example, in the example shown in the Figures, the chest section 18 includes a first foam core 54 and the shoulder section 20 includes a second foam core 56. The adjectives "first" and "second" with reference to the foam cores are used as identifiers and do not indicate order nor importance. The covering 52 is flexible relative to the first foam core 54 and the second foam core 56, and the covering 52 takes the shape of the first foam core 54 and the second foam core 56. The first foam core 54 defines the shape of the back 24, the legs 26, and the cavity 50.

The first foam core 54 and the second foam core 56 may be polyurethane foam, or any other suitable material type. The material type of the first foam core 54 may be the same as or different than the material type of the second foam core

56. The first foam core 54 may have the same compressibility or different compressibility than the second foam core 56.

The covering 52 includes an outer surface 58 and an inner surface 60. The inner surface 58 of the covering 52 faces the occupant and the outer surface 60 of the covering 52 faces away from the occupant when the seatbelt attachment 10 is attached to the shoulder belt 30 and the seatbelt assembly 14 is buckled. The inner surface 58 of the covering 52 includes the inner surface 48 of the back 24, and the outer surface 60 of the covering 52 includes the outer surface 46 of the back 24.

The covering 52 may be cloth, leather, vinyl (e.g., faux leather), or any other suitable material. The covering 52 may include a first panel 62 and a second panel 64 each elongated along the axes AC, AS of the chest section 18 and the shoulder section 20. The first panel 62 and the second panel 64 may be directly connected to each other along the axes AC, AS of the chest section 18 and the shoulder section 20, e.g., with stitching, adhesive, bonding, welding, etc. A joint line 70 between the first panel 62 and the second panel 64 is identified in FIGS. 3-6, and first panel 62 and the second panel 64 are joined at the joint line 70 by, for example, stitching, adhesive, bonding, etc. The first panel 62 may face away from the occupant and the second panel 64 may face the occupant when the seatbelt attachment 10 is attached to the shoulder belt 30 and the seatbelt assembly 14 is buckled. The first panel 62 may include the outer surface 46 of the chest section 18 including the outer surface 46 of the back 24 and the legs 26, and the second panel 64 may include the inner surface 48 of the chest section 18 including the inner surface 48 of the back 24 and the legs 26. The shoulder belt 30 abuts the covering 52 at the outer surface 46 of the back 24 when the seatbelt attachment 10 is attached to the shoulder belt 30.

The coefficient of friction of the outer surface 46 may be less than the coefficient of friction of the inner surface 48. This generates friction between the seatbelt attachment 10 and the body of the occupant to reduce sliding of the seatbelt attachment 10 relative to the body of the occupant, e.g., relative to a healing incision, and generates relatively less friction between the shoulder belt 30 and the seatbelt attachment 10 to allow for easier adjustment of the shoulder belt 30 relative to the seatbelt attachment 10, e.g., during buckling of the seatbelt assembly 14.

In some examples, the first panel 62 and the second panel 64 may have surfaces having different surface characteristics to accomplish the difference in coefficient of friction. As an example, the first panel 62 and the second panel 64 may be different material types providing different coefficient of friction. As one example, the first panel 62 may be smooth leather or smooth faux leather, and the second panel 64 may be leather with a napped surface (e.g., suede) or faux leather with a napped surface.

As set forth above, the seatbelt attachment 10 includes a joint 22 connecting the chest section 18 and the shoulder section 20. The joint 22 separates the chest section 18 from the shoulder section 20 along the shoulder-belt axis AB. In other words, the chest section 18 and the shoulder section 20 are end-to-end longitudinally along the shoulder-belt axis AB with the joint 22 longitudinally separating the chest section 18 and the shoulder section 20. The bottom end 38 of the chest section 18 is between the top end 40 of the chest section 18 and the lap belt 42. The joint 22 is at the top end 40 of the chest section 18. The shoulder section 20 extends from the joint 22 in the upward direction U along the shoulder-belt axis AB. In the example shown in the Figures, the joint 22 abuts both the shoulder section 20 and the chest section 18, and the joint 22 is compressed between the shoulder section 20 and the chest section 18 such that the top end 40 of the chest section 18 abuts the chest section 18 and the shoulder section 20 extends from the top end 40 of the chest section 18 and the joint 22 in the upward direction U.

The joint 22 is flexible relative to the chest section 18 and the shoulder section 20. Specifically, the second foam core 56 is moveable relative to the first foam core 54 about the joint 22. The joint 22 bends as the chest section 18 and the shoulder section 20. The joint 22 has a rotational axis R that is transverse to the chest-section axis AC and the shoulder-section axis AS. The rotational axis R of the joint 22 is nonparallel to the axis of the shoulder belt 30. The chest section 18 and the shoulder section 20 may maintain their shape as the chest section 18 and the shoulder section 20 rotate about the joint 22.

The joint 22 may be a portion of the covering 52 between the chest section 18 and the shoulder section 20, e.g., between the first foam core 54 and the second foam core 56. As an example, the first panel 62 and the second panel 64 may be connected between the first foam core 54 and the second foam core 56 to form the joint 22. In such examples, the first panel 62 and the second panel 64 may be stitched, adhered, bonded, welded, etc., at the joint 22.

The joint 22 is designed to be at a collar bone of an occupant. For example, the chest section 18 and the shoulder section 20 have relative lengths that allow the chest section 18 to be at the chest of the occupant and the shoulder section 20 to be at the shoulder of the occupant with the joint 22 at the collar bone of the occupant. Since the joint 22 is flexible relative to the chest section 18 and the shoulder section 20, the seatbelt attachment 10 bends at the joint 22, e.g., at the collar bone of the occupant. When the seatbelt attachment 10 bends at the joint 22, the chest-section axis AC is nonparallel to the shoulder-section axis AS. The bend of the seatbelt attachment 10 at the collar bone allows the seatbelt attachment 10 to conform to the shape of the body of the occupant, and to deform to a variety of body shapes and sizes of various occupants. The design of the seatbelt attachment 10 to conform to the shape of the body of the occupant aids in securing the seatbelt attachment 10 relative to the body of the occupant and limits the likelihood of sliding of the seatbelt attachment 10 relative to the body, e.g., relative to a healing incision.

In some examples, the seatbelt assembly 14 may include an insert 66 in the cavity 50. In such examples, the insert is removeable, i.e., the insert 66 can be inserted into the cavity 50 and removed from the cavity 50 by hand without a tool and without damage or destruction of the chest section 18 or the insert 66. The insert 66 may be selectively inserted into or removed from the cavity 50 by the occupant based on desired comfort level. For example, the insert 66 may aid in resisting movement of the chest section 18 relative to the occupant and/or may generate light compression against the body, e.g., at a healing incision, which may be comfortable to some occupants.

In examples including the insert 66, the insert 66 is compressible relative to the chest section 18. In other words, the insert compresses more readily than the chest section 18. When inserted into and removed from the chest section 18, the insert 66 deforms relative to the chest section 18. The insert 66 may be retained in the cavity 50 by friction fit.

The seatbelt attachment 10 is releasably engageable with the shoulder belt 30. The seatbelt attachment 10 may be selectively engaged to and removed from any one of the seatbelt assemblies that has a shoulder belt 30. The seatbelt attachment 10 includes a connector that releasably engages the shoulder belt 30. As an example, seatbelt assembly 14 includes a fastener 68 configured to fasten the seatbelt attachment 10 to the shoulder belt 30. In the example shown in the Figures, the fastener 68 includes straps extending from the shoulder section 20 and the chest section 18. The straps are flexible relative to the shoulder section 20 and the chest section 18 so that the straps can be opened to receive the shoulder belt 30 and closed over the shoulder belt 30. In the example shown in the Figures, the straps, the shoulder section 20, and the chest section 18 have hook and loop fasteners to secure a free end 72 of the strap to the shoulder section 20/chest section 18. In other examples, the free end 72 of the strap may be fastened to the shoulder section 20/chest section 18 with a snap, clip, cord, etc.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

What is claimed is:

1. A seatbelt assembly comprising: webbing including a shoulder belt elongated along an axis; and a seatbelt attachment releasably engageable with the shoulder belt; the seatbelt attachment including a chest section extending along the axis and a shoulder section extending along the axis; the seatbelt attachment including a joint connecting the chest section and the shoulder section, the joint being flexible relative to the chest section and the shoulder section; the shoulder section including a back elongated along the axis; the shoulder section including two legs elongated along the axis and aligned along the axis with the back, the legs each having a distal end and the legs extending away from each other from the back to the distal ends, respectively.

2. The seatbelt assembly of claim 1, wherein the chest section includes a first foam core and the shoulder section includes a second foam core moveable relative to the first foam core about the joint.

3. The seatbelt assembly of claim 2, wherein the seatbelt attachment includes a covering over the first foam core and the second foam core, the joint being a portion of the covering between the first foam core and the second foam core.

4. The seatbelt assembly as set forth in claim 1, wherein the joint separates the chest section from the shoulder section along the axis.

5. The seatbelt assembly of claim 1, wherein the joint has a rotational axis that is nonparallel to the axis of the shoulder belt.

6. The seatbelt assembly of claim 1, wherein:
the chest section has a chest-section axis on which the chest section is elongated;
the shoulder section has a shoulder-section axis on which the shoulder section is elongated; and
the joint has a rotational axis that is transverse to the chest-section axis and the shoulder-section axis.

7. The seatbelt assembly as set forth in claim 1, wherein the chest section and the shoulder section extend from the shoulder belt in a body direction, the shoulder section is thinner than the chest section in the body direction.

8. The seatbelt assembly as set forth in claim 1, wherein:
the back includes an outer surface and an inner surface opposite the outer surface;

the distal ends of the legs are spaced from each other defining a cavity along the inner surface of the back; and the shoulder belt abuts the outer surface of the back.

9. The seatbelt assembly as set forth in claim 8, wherein the coefficient of friction of the outer surface is less than the coefficient of friction of the inner surface.

10. The seatbelt assembly as set forth in claim 8, further comprising a removeable insert in the cavity.

11. The seatbelt assembly as set forth in claim 1, further comprising a fastener on the back, the fastener releasably engaging the shoulder belt.

12. The seatbelt assembly as set forth in claim 1, wherein the chest section is elongated in an upward direction along the axis from a bottom end to a top end, the shoulder section extending from the top end in the upward direction along the axis.

13. The seatbelt assembly as set forth in claim 12, wherein the joint is designed to be at a collar bone of a vehicle occupant.

14. The seatbelt assembly as set forth in claim 1, wherein the legs being the same length as each other from the back to the distal ends, respectively.

15. A seatbelt attachment comprising:

a chest section having a chest-section axis on which the chest section is elongated;

a shoulder section having a shoulder-section axis on which the shoulder section is elongated; and a joint connecting the chest section and the shoulder section, the joint being flexible relative to the chest section and the shoulder section;

the joint having a rotational axis that is transverse to the chest-section axis and the shoulder-section axis;

the shoulder section including a back elongated along the shoulder-section axis, the back including an outer surface and an inner surface opposite the outer surface;

the shoulder section including two legs elongated along the shoulder-section axis and aligned along the shoulder-section axis with the back, the legs each having a distal end and the legs extending from the back to the distal ends, respectively;

the distal ends of the legs being spaced from each other defining a cavity along the inner surface of the back; and the coefficient of friction of the outer surface being less than the coefficient of friction of the inner surface.

16. The seatbelt attachment of claim 15, wherein the chest section includes a first foam core and the shoulder section includes a second foam core moveable relative to the first foam core about the joint; and further comprising a covering over the first foam core and the second foam core, the joint being a portion of the covering between the first foam core and the second foam core.

17. A seatbelt assembly comprising:

webbing including a shoulder belt elongated along an axis; and a seatbelt attachment releasably engageable with the shoulder belt;

the seatbelt attachment including a chest section extending along the axis and a shoulder section extending along the axis;

the seatbelt attachment including a joint connecting the chest section and the shoulder section, the joint being flexible relative to the chest section and the shoulder section;

the shoulder section including a back elongated along the axis, the back including an outer surface and an inner surface opposite the outer surface;

the shoulder section including two legs elongated along the axis and aligned along the axis with the back, the legs each having a distal end and the legs extending from the back to the distal ends, respectively;

the distal ends of the legs being spaced from each other defining a cavity along the inner surface of the back;

the shoulder belt abutting the outer surface of the back; and the coefficient of friction of the outer surface being less than the coefficient of friction of the inner surface.

18. The seatbelt assembly as set forth in claim 17, wherein the joint separates the chest section from the shoulder section along the axis.

19. The seatbelt assembly of claim 17, wherein the joint has a rotational axis that is nonparallel to the axis of the shoulder belt.

20. The seatbelt assembly as set forth in claim 17, wherein the joint is designed to be at a collar bone of a vehicle occupant.

* * * * *